United States Patent [19]

Staendeke

[11] 4,173,578
[45] Nov. 6, 1979

[54] PRODUCTION OF ALKENYL PHOSPHINIC ACIDS

[75] Inventor: Horst Staendeke, Erftstadt, Fed. Rep. of Germany

[73] Assignee: Hoechst Aktiengesellschaft, Fed. Rep. of Germany

[21] Appl. No.: 840,908

[22] Filed: Oct. 11, 1977

[30] Foreign Application Priority Data

Oct. 15, 1976 [DE] Fed. Rep. of Germany ....... 2646582

[51] Int. Cl.² .............................................. C07F 9/30
[52] U.S. Cl. .......................... 260/502.4 R; 260/652 R
[58] Field of Search ................................. 260/502.4 R

[56] References Cited

U.S. PATENT DOCUMENTS 3,787,486 1/1974 Randall et al. ................ 260/502.4 R

OTHER PUBLICATIONS

Canaran et al., "J. Chem. Soc.", (1962), pp. 331–334.
Berlin et al., "J. Org. Chem.", (1965), pp. 2745–2748.

Primary Examiner—Joseph E. Evans
Attorney, Agent, or Firm—Connolly and Hutz

[57] ABSTRACT

Production of alkenyl phosphinic acids of the general formula:

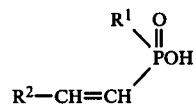

in which $R^1$ stands for an alkyl, aralkyl, cycloalkyl or aryl group having 1 to 20 carbon atoms, and $R^2$ stands for hydrogen or an alkyl group having 1 to 4 carbon atoms. The compounds are made by subjecting a 2-halogenoalkyl phosphinic acid-2-halogenoalkyl ester of the general formula:

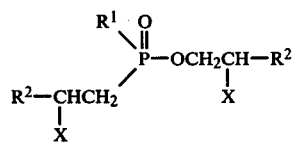

in which $R^1$ and $R^2$ have the meanings given above, and X stands for a halogen atom, to thermal decomposition.

6 Claims, No Drawings

PRODUCTION OF ALKENYL PHOSPHINIC ACIDS

This invention relates to a process for making alkenyl phosphinic acids of the general formula

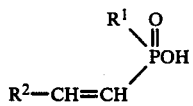

in which $R^1$ stands for an alkyl, aralkyl, cycloalkyl or aryl group having approximately 1 to 20 carbon atoms, and $R^2$ stands for an alkyl group having approximately 1 to 4 carbon atoms.

Alkenyl phosphinic acids are intermediate products which are used for the production of flame-retardant agents, stabilizers for plastic materials, plant protective agents, and corrosion inhibitors.

It is known that vinylphenyl phosphinic acid can be made by subjecting a vinylphenyl phosphinic acid ethyl ester or chloride to hydrolysis (cf. G. M. Kosolapoff/L. Maier, Organic Phosphorus Compounds, vol. 6, Wiley Interscience, New York (1973)). A process for making vinyl phosphinic acids has been disclosed in German Patent Specification "Offenlegungsschrift" 2.344.332, wherein a 2-hydroxyethyl phosphinic acid is dehydrated.

These prior processes are however not satisfactory inasmuch as very expensive starting materials, which have to be produced by a plurality of processing steps, are used therein.

The present invention now unexpectedly provides a process for making alkenyl phosphinic acids of the above general formula I, which comprises subjecting a 2-halogenoalkyl phosphinic acid-2-halogenoalkyl ester of the following general formula II

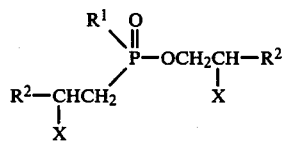

in which $R^1$ and $R^2$ have the same meanings as in formula I, and X stands for a halogen atom, to thermal decomposition.

In a preferred version of the present process, the 2-halogenoalkyl phosphinic acid-2-halogenoalkyl ester of formula II in a stream of inert gas is heated to 150° to 300° C., and resulting 1,2-dihalogenoalkane is simultaneously separated from the reaction mixture.

It is more particularly good practice to separate the 1,2-dihalogenalkane by distillation under reduced pressure, if desired.

The starting materials which are useful in the present process may more preferably be selected from those compounds of the above formula II, in which X stands for a chlorine or bromine atom. These comprise, e.g. the following esters:

methyl-2-chloroethyl phosphinic acid-2-chloroethyl ester,
ethyl-2-chloroethyl phosphinic acid-2-chloroethyl ester,
phenyl-2-chloroethyl phosphinic acid-2-chloroethyl ester,
methyl-2-chloropropyl phosphinic acid-2-chloropropyl ester,
ethyl-2-chloropropyl phosphinic acid-2-chloropropyl ester, or
phenyl-2-chloropropyl phosphinic acid-2-chloropropyl ester.

It is also preferable in the process of this invention to initially heat the starting material until 1,2-dihalogenoalkane ceases to be evolved and then to repeat this procedure after the introduction of a hydrogen halide, the hydrogen halide being preferably used in a proportion of approximately 0.2 to 3 mols per mol of 2-halogenoalkyl phosphinic acid-2-halogenoalkyl ester.

The present process compares favorably with the prior art methods as it uses a 2-halogenoalkyl-phosphinic acid-2-halogenoalkyl ester as the starting material, which is readily obtainable by reacting a phosphonous acid dihalide with an epoxy alkane and subjecting the resulting product to thermal isomerization, as shown e.g. by the following equations:

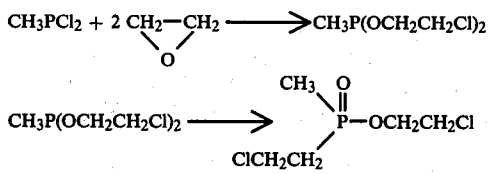

These reactions are technically easy to effect and produce the desired product in very good yields. (Houben-Weyl: Methoden der organischen Chemie, vol. XII/1; Organische Phosphorverbindungen, published by G. Thieme Verlag, Stuttgart (1963); and G. M. Kosolapoff/L. Maier, Organic Phosphorus Compounds, vol. 4, Wiley Interscience, New York (1972)).

The reactions, which take place in the process of the present invention, can be illustrated e.g. by the following equations:

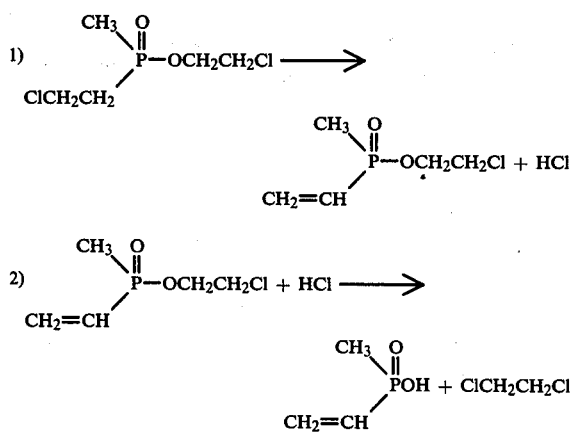

The following Examples are intended to further illustrate the process of this invention.

EXAMPLE 1

278 g (1.40 mols) of 2-chloroethylmethyl phosphinic acid-2-chloroethyl ester was placed in a reactor comprising a 500 ml three-necked flask provided with a thermometer, gas inlet and distillation bridge (ice water cooling), the latter being provided with a thermometer and receiver, and heated therein to 200° C. while nitrogen was passed through at a rate of 10 l/h.

After 2 hours, 109 g (1.10 mols) of dichloroethane was found to have distilled over.

The distillation residue (164 g) was subjected to NMR-spectroscopy and found to be composed of:
- 65 weight% of vinylmethyl-phosphinic acid
- 23 weight% of vinylmethyl-phosphinic acid-2-chloroethyl ester and
- 12 weight% of other phosphorus compounds.

This corresponds to a yield of 107 g (72% of the theoretical) of vinylmethyl-phosphinic acid.

EXAMPLE 2

314 g (1.53 mols) of 2-chloroethylmethyl phosphinic acid-2-chloroethyl ester was placed in the apparatus described in Example 1, heated therein to 200° C., initially for 1.5 hours while nitrogen was passed through at a rate of 10 l/h and then for a further 1.5 hours while gaseous hydrogen chloride was passed through at a rate of 15 l/h. After the experiment had been terminated, 142 g (1.43 mols) of dichloroethane was found to have distilled over.

The distillation residue (178 g) was subjected to NMR-spectroscopy and found to be composed of:
- 77 weight% of vinylmethyl phosphinic acid,
- 11 weight% of vinylmethyl phospinic acid-2-chloroethyl ester, and
- 12 weight% of other phosphorus compounds.

This corresponded to a yield of 137 g (85% of the theoretical) of vinylmethyl phosphinic acid.

I claim:

1. A process for making alkenyl phosphinic acids of the general formula

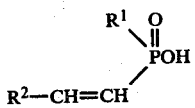

in which $R^1$ stands for an alkyl, aralkyl, cycloalkyl or aryl group having 1 to 20 carbon atoms, and $R^2$ stands for hydrogen or an alkyl group having 1 to 4 carbon atoms, which comprises subjecting a 2-halogenoalkyl phosphinic acid-2-halogenoalkyl ester of the general formula

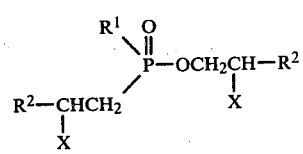

in which $R^1$ and $R^2$ have the meanings given above, and X stands for a halogen atom, to thermal decomposition by heating in a stream of inert gas at temperatures of 150° to 300° C. and simultaneously separating the resulting 1,2-dihalogenoalkane.

2. The process as claimed in claim 1, wherein the 1,2-dihalogenoalkane is separated by distillation, if desired, under reduced pressure.

3. The process as claimed in claim 1, wherein the 2-halogenoalkyl phosphinic acid-2-halogenoalkyl ester is selected from those compounds of formula II, in which X stands for a chlorine or bromine atom.

4. The process as claimed in claim 3, wherein the methyl-2-chloroethyl phosphinic acid-2-chloroethyl ester;
ethyl-2-chloroethyl phosphinic acid-2-chloroethyl ester;
phenyl-2-chloroethyl phosphinic acid-2-chloroethyl ester;
methyl-2-chloropropyl phosphinic acid-2-chloropropyl ester;
ethyl-2-chloropropyl phosphinic acid-2-chloropropyl ester or
phenyl-2-chloropropyl phosphinic acid-2-chloropropyl ester is used.

5. The process as claimed in claim 1, wherein the starting materials are initially heated until 1,2-dihalogenoalkane ceases to be evolved, and the heating is repeated, after the introduction of a hydrogen halide.

6. The process as claimed in claim 5, wherein 0.2 to 3 mols of hydrogen halide is used per mol of 2-halogenoalkyl phosphinic acid-2-halogenoalkyl ester.

* * * * *